(12) United States Patent
Silvers

(10) Patent No.: US 6,404,779 B1
(45) Date of Patent: Jun. 11, 2002

(54) SYSTEM AND METHOD OF DISHARMONIC FREQUENCY MULTIPLEXING

(75) Inventor: John Leroy Silvers, Fort Lauderdale, FL (US)

(73) Assignee: Bandwidth Technology Corp., New York, NY (US)

( * ) Notice: Subject to any disclaimer, the term of this patent is extended or adjusted under 35 U.S.C. 154(b) by 0 days.

(21) Appl. No.: 09/120,448

(22) Filed: Jul. 22, 1998

Related U.S. Application Data

(60) Provisional application No. 60/061,334, filed on Oct. 8, 1997.

(51) Int. Cl.[7] .................................................. H04J 1/02
(52) U.S. Cl. ...................................... 370/493; 370/537
(58) Field of Search ................................ 370/282, 286, 370/295, 430, 480, 481, 482, 487, 490, 493, 494, 495, 532, 536, 537, 538, 542, 543, 535, 352, 353, 354, 355, 356

(56) References Cited

U.S. PATENT DOCUMENTS 4,178,823 A * 12/1979 McCoskey et al. ............ 84/672
5,581,651 A * 12/1996 Ishino et al. ................. 704/205

* cited by examiner

*Primary Examiner*—Kwang B. Yao
(74) *Attorney, Agent, or Firm*—Hopgood, Calimafde, Judlowe & Mondolino, LLP

(57) ABSTRACT

A multiplexing system and method for conveying simultaneously a multiplicity of digital communication channels over a single transmission medium. Multiplexing is effected by transforming the digital bitstream of each incoming channel to a digitally-represented sound bitstream and transmitting all of the digitally-represented sound bitstreams over the single medium. Digital bitstreams carried on each incoming channel entering the system which are in the form of binary "on" and "off" bits, are converted into a digital stream of corresponding sound bits. Each sound bitstream is rendered distinctive and non-interfering with other streams during simultaneous transmission over the common medium by having the digitally-represented sound bits of each bitstream derived from a unique prime number Hertz frequency. Expanded bandwidth is accomplished by grouping the sound bitstreams into a "chord" of disharmonic frequencies, and then transmitting the chord composed of several discordant sound bitstreams over the single transmission medium.

13 Claims, 2 Drawing Sheets

SYSTEM AND METHOD OF DISHARMONIC FREQUENCY MULTIPLEXING

RELATED APPLICATION

This application is related to my provisional application Ser. No. 60/061,334, filed Oct. 8, 1997, having the same title, the entire disclosure of which is incorporated herein by reference.

BACKGROUND OF INVENTION

1. Field of Invention

This invention relates generally to communication multiplexing, and more particularly to a system and method facilitating simultaneous transmission of a multiplicity of channels of digital information over a common channel.

2. Status of Prior Art

Communication: The first copper-wire communication system was only capable of carrying one message per wire. Communication companies soon realized that in order to enlarge their capacity to carry messages they would have to devise ways to transmit several messages simultaneously over a single wire, for the cost of installing additional lines to accommodate increased demand was high. Companies that could reduce costs by putting more and more information over a single line, would have a competitive advantage. Discoveries made in transmission methods allowing more than one message to be transmitted per line then permitted the telegraph and telephone industry to become viable commercial enterprises. The same challenge of maximizing bandwidth and increasing line capacity which prevailed from the beginning of telecommunications still exists in modern communication technology.

Today, telecommunication networks provide the primary means for conveying voice and data traffic between sources and destinations. But existing telecommunication networks cannot handle the increasing demand for higher and higher transmission capacity. Rising population, lower telephone rates and increased data traffic over the Internet, all underscore the need to increase network capacity. As bandwidth becomes more available, higher bandwidth applications are quickly developed, such as higher resolution web pages and video-on-demand, which once again heightens the demand for bandwidth.

One way to satisfy an increasing demand for bandwidth is by installing additional transmission lines or by placing additional satellites in the sky. Both solutions are exceptionally expensive and dictate substantial investments. Yet even satellite solutions have limitations, for there is only a limited number of satellites that can be placed in the ideal transmission location directly above the North Pole. Wireless systems, where the available radio spectrum is limited, also rely on bandwidth utilization or compression methods to enlarge the capacity of the system. To remain competitive, network service providers must endeavor to preserve the functionality of their existing networks, yet still be able to accommodate the increasing bandwidth demand to handle voice, data, and video transmission.

In conventional analog transmission, voice energy acts to compress the carbon granules in a microphone, thereby varying the microphones resistance to electrical current. Then the varying current, which is analogous to the speaker's voice, is used to energize an electromagnet actuating a diaphragm which vibrates to reproducing the original voice. Digital transmission adds several steps to this transformation, for the voice is converted to an electrical current pattern whose varying amplitude is measured thousands of times per second. These measurements are encoded as binary numbers, consisting of "0" and "1"s.

Unlike analog transmission which conveys the sound as a continuous wave form, in digital transmission binary numbers are transmitted in representational encoding schemes. Binary digits or bits, may be transmitted singly, as discrete, on-off or zero/non-zero current pulses, or in groups as simultaneous pulses at different frequencies. At the receiving end, the bitstream is interpreted and the numbers reconstituted to modulate a current which drives a speaker. This method is "digital" because it entails conversion of an analog signal to numbers, and the transmission of digits in symbolic form.

Compression: There are several known methods which make possible the transmission of information with diminished bandwidth requirements. The most widely employed method relating to "compression" uses mathematical algorithms and dictionary tables to manipulate and "point" digital signals in such a way that each transmission channel uses less bandwidth to carry recognizable information. Compression is achieved by building a predictive model of the waveform, removing unnecessary elements, and reconstructing the wave form from the remaining elements.

When converting an analog signal into digital form, accurate conversion requires at least twice as many measurements (samples per second), as the highest frequency in the signal. The human voice generates sound frequencies in zero to 4,000 Hz range. Hence an ideal digital voice circuit, accepting an input in the range of 0–4,000 Hz, must sample this signal 8,000 times per second. Each sample is represented by 8 bits of data, and a single voice circuit, referred to as DS0, "digital signal level zero", carries 64,000 (8,000× 8) bits of data.

Compression methods are based on reducing the number of bits capable of carrying a human voice or other data transmission. Currently used compression algorithms can produce acceptable voice quality using less than 64 kbs by eliminating unnecessary frequencies, particularly all those below 300 Hz and those above 3,300 Hz, and emphasizing the frequencies in the 1,000 Hz range that carry most of the voice energy. Methods that drop an excessive amount of input signal tend to frustrate high-speed tonal data transmission schemes employed by modems and faxes. Currently employed compression algorithms and equipment are able to transmit acceptable voice quality with a compression ratio of 8:1, using 8,000 bps per channel.

With these compression methods, one channel can be made to carry eight voice conversations or eight fax transmission over a line that originally has able to carry only one voice conversation. Higher compression methods which transmit voice and data over a circuit using less than 8,000 bps, suffer from increasing degradation of voice quality and "loss," whereby at the receiving end of the line the voice in its original form is not clearly heard. Although new methods and algorithms may be employed to allow for clear voice transmission using less than 8,000 bps, there are appreciable limitations to these methods. All compression methods using algorithms suffer from greater and greater "loss" as compression ratios increase. Fax and video transmission that are more sensitive to bandwidth degradations are more limited in their acceptable compression ratios.

While the main advantage of digital compression is that it increases network efficiency, it can in some situations reduce it. Users of compression technology must ensure that their chosen compression method has the ability to transmit compressed data at the full capacity of the transmission lines. If not, consideration must be given to downgrading the speed of the transmission lines and sacrificing some of the throughput. Furthermore, the amount of time the computer spends compressing and decompressing the data can reduce efficiency.

Multiplexing: The most common form of telecommunications service is T-1 protocol. T-1 uses a form of multiplexing in which 24 voice or data channels, each with 8,000 bps, can simultaneously exist on one pair of twisted copper wires. The total bandwidth capacity of T-1 is 1.544 Mbps. Compression methods are used in conjunction with T-1 and other transmission protocols to maximize bandwidth. Common compression systems using a ratio of 8:1, can carry 192 simultaneous voice or data channels (24×8) over a T-1.

Network service providers employ methods for increasing bandwidth by use of compression and multiplexing, the most common multiplexed line being T-1. Conversations or the digital information carried on each T-1 line or channel, is rendered unique, and transmitted with other channels over a common medium by multiplexing.

An early method used by phone companies to render channels unique, is Frequency Division Multiplexing (FDM). In FDM, each of the 24 channels are rendered distinct by having each channel assigned to a frequency band. (For example, line 1 would use the frequency band of 0 Hz–4,000 Hz, line 2 would use the 4,000 Hz–8,000 Hz band, etc.) But this method is best suited for analog signals which are subject to degradation and noise interference, and is therefore now rarely used. Common techniques used today are Time Division Multiplexing (TDM) and Statistical Multiplexing (STDM), often called "Packet switching." In TDM, each of the 24 channels (or lines) are rendered distinct by having each channel assigned to a particular, non-overlapping time slot. Frames of 24 time slots are transmitted, in which Channel 1 gets the first time slot in the frame, Channel 2 gets the second time slot and so on. STDM works in a similar manner to TDM, assigning channels on the basis of time division. But it takes advantage of statistical fluctuations, and instead of automatically assigning each channel to a time slot, STDM assigns only active channels to time slots. Hence, instead of transmitting channels in sequential order (1, 2, 3, 4, 5, 6) as in TDM, STDM only assigns time slots to channels that are being used, e.g., 1, 3, 1, 5, 1, 6 etc. This method creates higher bandwidth utilization than TDM.

SUMMARY OF INVENTION

In view of the foregoing, the main object of this invention is to provide a multiplexing system and method for increasing the available bandwidth of transmission media including wire and wireless transmission, as well as satellite and fiber optics communication networks.

More particularly, an object of this invention is to provide a system and method in which multiplexing of a multiplicity of incoming digital signals over a common transmission line is effected by Prime Frequency Multiplexing (PFM), wherein each channel transmitted over the common line is rendered distinctive to avoid interference with any other channel.

A significant feature of a PFM system and method in accordance with the invention is that each channel is rendered distinctive by assigning to the digital information contained therein a unique prime number Hertz frequency. Since no prime number is divisible by any other number, and the prime numbers assigned to the respective channels are not harmonically related, interference or cross talk therebetween is avoided even though the multiplicity of signals are simultaneously conveyed over the common line.

Briefly stated, these objects are attained by a multiplexing system and method for conveying simultaneously a multiplicity of simultaneous digital communication channels over a single transmission medium. Multiplexing is effected by transforming the digital bitstream of each incoming channel to a digitally-represented sound bitstream and transmitting all of the digitally-represented sound bitstreams over the single medium. Digital bitstreams carried on each incoming channel entering the system in the form of binary "on"-"off" signals, are converted into a digital stream of corresponding sound bits. Each sound bitstream is rendered distinctive and non-interfering with other streams during simultaneous transmission over a common medium by having the digitally-represented sound bits of each bitstream derived from a unique prime number Hertz frequency. Expanded bandwidth is accomplished by grouping the sound bitstreams into a "chord" of disharmonic frequencies, and then transmitting that chord containing the several discordant sound bitstreams over the single transmission medium.

At the receiving end, a decoder is programmed to receive the information carried by the prime frequency corresponding to the original sending line. This enables each individual stream of binary sound information to be separated from the "chord" and once again restored to a digital stream of information corresponding to the original digital stream.

The advantage of prime frequency multiplexing (PFM) is that it is not limited by time nor does it depend on a specific transmission medium. PFM can generate a greater number of distinct channels over electronically-based transmission media than multiplexing and compression systems heretofore known. Using PFM and the extra bandwidth it makes available, higher bit sampling can be effected and therefore greater fidelity in transmission. The common practice of telephone companies is to use a digital coding processor that take 8,000 samples per second at 8 bits, for a total of 64,000 bps. This number of bits per second is adequate for reproduction of a human voice. PFM can be programmed to code for the limits of the human ear which exceeds 12,000 Hz, rather than the human voice. Digitizing can be accomplished by taking 22,000+ samples, at 16 bits, for a total of 356,000+ bits per second. This can yield music of CD ROM quality over an existing telephone or data line.

BRIEF DESCRIPTION OF DRAWINGS

For a better understanding of the invention, as well as other objects and features thereof, reference is made to the accompanying drawings wherein.

DESCRIPTION OF INVENTION

A multiplexing system and method in accordance with the invention acts to expand the bandwidth capacity of existing digital transmission or storage media by simultaneously transmitting a plurality of streams of disharmonic, binary-coded, digitally-represented sound bits of information.

In an embodiment of the invention relating to the increased capacity to transmit digital information over a standard transmission medium, the incoming information from each channel entering the system as a bitstream of binary coded information ("0"s and "1"s), is transformed to an equivalent coding in which "0"="no-play" and "1"= "play", derived from a prime number Hertz frequency. A prime number is a positive integer having no divisor except itself and the integer 1. Thus the number 31 is a prime number, whereas the number 30 is not.

A method in accordance with the invention can be used with any transmission medium capable of carrying or transmitting a binary stream of information. Such transmission media includes copper wire, satellite transmission, fiber optics, etc. and such protocols as T-1, ATM, Frame Relay, etc. A method in accordance with the invention will work with any digital information capable of being transmitted or stored, such as data, image, video or voice applications.

Figure 1:
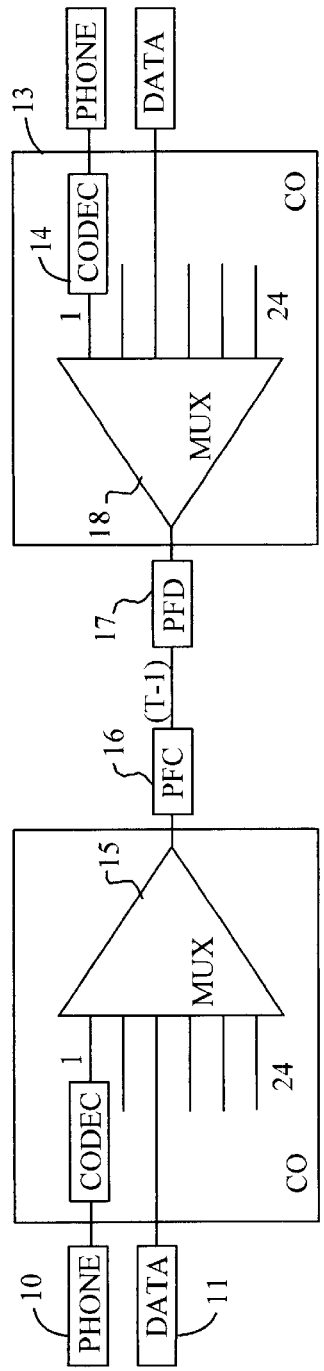
FIG. 1 is a block diagram of a telecommunications network in accordance with the invention.

FIG. 1 is a block diagram of a portion of a telecommunications network which includes a typical transmission scheme now employed by most telecommunications companies. Box 10 labeled as "PHONE," represents a standard analog telephone in a user's location. Box 11, labeled "DATA," represents a computer or any device other transmitting digital information. Box 13 labeled "CO" represents the Central Office, which is the physical location of the local phone company that contains the main switching equipment that connects all the users in the local area.

One piece of equipment contained in the CO switch, consists of a telecommunications device known as a CODEC. Box 14 labeled "CODEC" represents the unit within the phone switch that converts the incoming analog signal (in the form of a sound wave) to a digital signal (in the form of binary on/off, or 0/1 signals).

Information coming into the CODEC from a DATA line is in a digital format and does not need an analog to digital conversion. The digital signal of each incoming line is connected to the 24 MUX. Box 15 labeled "24 MUX" is a standard piece of telecommunications equipment that converges the 24 incoming digital lines into one outgoing line, while maintaining each of the 24 lines as distinct voice or data channels. The line labeled "T-1" represents a T-1 transmission protocol, this being the most commonly employed protocol in telephony.

Box 16 labeled "PFC" (Prime Frequency Coder) is a digital signal converter that converts binary digital signals to the corresponding digitally-represented sound bits ("play" and "no-play"), and transmits that signal over the connecting line to the "PFD" (Prime Frequency Decoder) in box 17. PFD 17 receives digitally-represented sound bits ("play" and "no-play") from PFC 16 and converts them to their corresponding digital signals (of "0"s and "1"s). Information is then transmitted through a 24 MUX (box 18) and CODEC 14 back to the user's phone.

Figure 2:
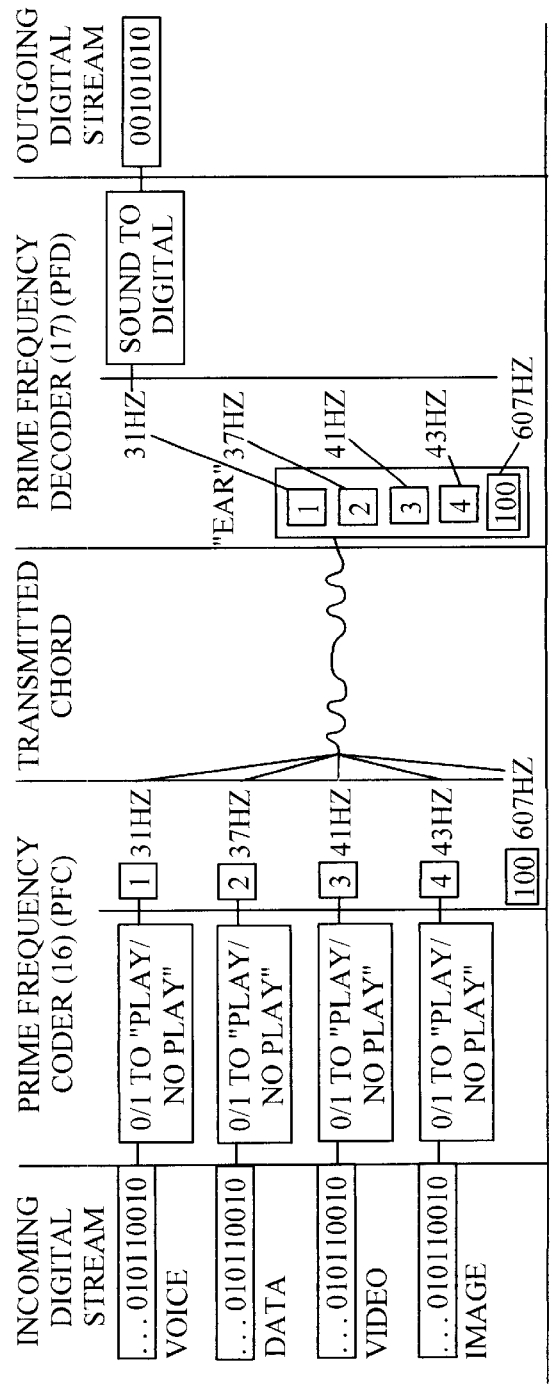
FIG. 2 is an enlarged block diagram of a portion of FIG. 1.

FIG. 2 is an enlarged block diagram of a portion of FIG. 1, illustrating the process and transformation that takes place within and between the PFC 16 and PFD 17. FIG. 2 shows with the programming and method related to the conversion of digital computer signaling (1/0) to digitally-represented sound signalling (play/no-play), as well as the reverse process, and the method of combining and simultaneously transferring a plurality of digitally-represented sound signals between the PFC and PFD in such a way that the transferred information contained in each channel remains distinctive and non-interfering.

The section of FIG. 2 labeled "INCOMING DIGITAL STREAM" is a representation of the incoming digital or binary bit stream in the form of "on/off" or "0/1" combinations, carried over the lines entering PFC 16. The incoming digital stream can carry any type of information capable of being translated into a digital format, including voice, music, data video frames, images, etc.

The section labeled "Prime Frequency Coder" (PFC-16) represents the system and its programming that changes the digital computer stream of information ("0"s and "1"s) to a digitally-represented sound stream of information ("play/no-play"). This process is accomplished by a computer software, a programmed computer chip, or software integrated within the hardware processing cards of a computer, router, or telecommunications switch.

Figure 3:
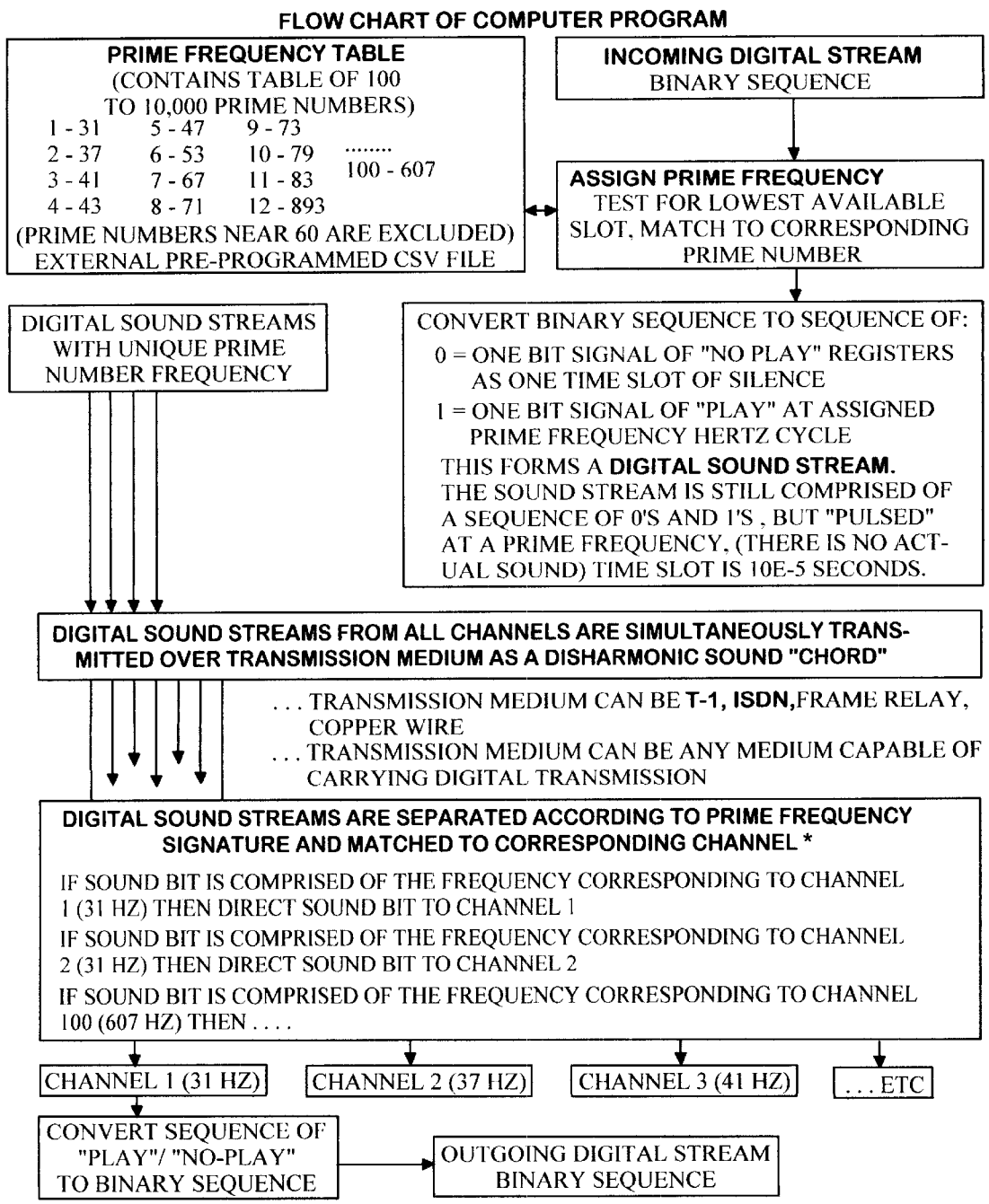
FIG. 3 is a preferred computer program for a system and method in accordance with the invention.

The flowchart for the computer program is shown in FIG. 3. The computer program contained in PFC 16 carries out the following operations:

(a.) It reads the digital stream (in the form of "0"s and "1"s) from each incoming voice or data line, (b.) It changes each bit of information in the incoming digital stream into a digitally-represented sound stream of corresponding bits of "play" and "no-play" signals. Each time the program receives a "0" from the incoming digital stream, it converts that signal to a silent or "no-play" bit signal. And each time the program receives a "1" from the incoming digital stream, it converts the "1" to a digitally-represented sound or "play" bit signal, (c.) It assigns each incoming digitally-represented sound stream, consisting of numerous bits of "play/no-play" commands, to a particular Hertz cycle frequency found in a particular location, or position number in the table of prime number frequencies.

In the embodiment of the invention illustrated in FIG. 2, in the Prime Frequency coder section, the first incoming digital stream of information is assigned to location or slot 1 in the table of prime number frequencies. With each no-play/play signal, the program generates a sound "bit" containing "silence" and a "bit" played out at the Hertz frequency of 31 cycles per second. In the same embodiment, the second digital stream of information is assigned to location or slot 2 in the table of prime number frequencies, and with each no-play/play signal, the program generates a sound "bit" containing "silence" and a "bit" containing the Hertz frequency of 37 cycles per second. In slot 3, the Hertz frequency is 41 Hz and is slot 4 it is 43 Hz.

(d.) It takes all the no-play/play bits from each incoming digitally-represented sound streams, and "plays out" each digitally-represented sound stream on its unique prime number frequency.

(e.) It combines these sound streams on a common transmission line and simultaneously transmits all of the digitally-represented sound streams over the transmission medium in the form of a disharmonic "chord" of multiple sounds, for the sounds are not harmonically related.

The software contained within the PFC and PFD devices of the system can be programmed to accommodate 10,000 or more incoming and outgoing lines, and it can be programmed to simultaneously transmit 10,000 or more channels of information.

In step (d.) above, the PFC programming and architecture acts in a similar manner to a telecommunications multiplexer (MUX), where it takes all the incoming digital sound streams, assigns each line to a unique channel, and then simultaneously routes them all over a common transmission medium. Multiplexing devices often separate or divide channels of information by allocating time or frequency ranges. In a system in accordance with the invention, channels are rendered unique by allocation of each channel to a Hertz frequency corresponding to a prime number. Hence there is no time or frequency range separation.

The intermediate section of FIG. 2, labeled "TRANSMITTED CHORD," represents the combination of all digitally-represented sound streams simultaneously transmitted over a common transmission medium in the form of a disharmonic "chord" of sound. It is "disharmonic" because all transmitted digitally-represented sound bits have respective prime number frequencies. Hence no transmitted frequency is able to cancel out or "harmonize" with any other frequency in the chord. In the transmitted chord, each digitally-represented sound stream is formed from digitized signals "play" or "no-play" on a particular prime Hz frequency.

The reason no prime number frequency can "harmonize" with any other prime number frequency is that to be a harmonic it must be a multiple of another frequency. Therefore even though 100 or 10,000 prime number digital streams are transmitted simultaneously across a single transmission medium, no digitally-represented sound stream will cancel out any other digitally-represented sound stream or interfere therewith. All digitally-represented sound streams will be transmitted over the transmission medium intact, with no loss of information. Transmission can also be accomplished over any medium, or protocol, for it is capable of transmitting digital information, such as T-1, frame relay, ATM, satellite, wireless, ISDN, fiber optic, regular copper wire, etc.

The section labeled "Prime Frequency Decoder" (PFD-17) represents a device and its programming that acts as a "digital ear," allowing each line to pick up or "hear" only the "play/no-play" digitally-represented sound stream of the specific prime frequency corresponding to its position in the prime frequency table.

This process can be accomplished with the use of 4 standard computer processing chips, or DSPs (Digital Signal Processors), each capable of a minimum of 10 MIPS. Once the particular digitally-represented sound stream is "heard" in accordance with its assigned line location, the PFD changes the digitally-represented sound stream of information ("play/no-play" ) back into the original sequence (of "0"s and "1"s) of the incoming digital computer stream. This process is accomplished by a computer software application contained within the software of a computer, a switching or routing device; or programmed into a computer chip and integrated within the hardware processing cards of a computer, router, or telecommunications switch.

PFD 17 restores or reverses the transformation carried out in PFC 16. The computer program contained in PFD 17 carries out the following operations:

(a.) It creates a digital "ear" that allows each receiving line to hear only the sound "bits" of the prime frequency of its corresponding sending line, (b.) It receives each prime Hz cycle, according to its corresponding position assignment in the prime number table, and renders the information transmitted on each prime frequency as a distinct channel which is linked to a single outgoing line. The PFD acts as a "deMUXer," where one line carrying all the frequencies in the disharmonic chord is received and then separated into a plurality of single lines. If 100 prime number frequencies are simultaneously sent over the transmission medium, the PFD separates each digital stream and routes each digital stream coming over a particular frequency, to its corresponding assignment in one of the 100 outgoing lines, (c.) It changes the incoming digitally-represented sound stream consisting of "play/no-play" signals into a digital computer stream of corresponding signals of "0"s and "1"s. Each time the program receives a digitally-represented sound bit, or "play" signal, from the incoming digitally-represented sound stream, it converts that signal to a "1," and each time the program receives a silent bit, or "no-play" signal, from the incoming digital stream, it converts that signal to a "0", (d.) It routes the restored digital information to its corresponding channel.

In the embodiment shown in FIG. 2, the first digital stream of information is received as a "play/no-play" signal, consisting of sound "bits" made up of the Hertz frequency of 31 cycles per second. The portion of the PFD, corresponding to line 1, can only hear a 31 Hz sound. It can hear no other sound transmitted in the chord. The portion of the PFD, corresponding to line 2, can only hear sound transmitted at 37 Hz. Hence, the digitally-represented sound stream contained in the first incoming line (transmitted at 31 Hz) is picked up by the PFD, changed to a computer digital stream (0/1), and routed as digital information over the first outgoing line.

The digitally-represented sound stream contained in second incoming line (transmitted at 37 Hz) is picked up by PFD 17, changed to a computer digital stream (0/1), and routed as digital information over the second outgoing line, and so on with the other lines.

This invention can be used to increase bandwidth capacity on existing transmission lines and with satellite transmission protocols. This invention has the following advantages:

(a.) No other multiplexing or compression method uses prime number frequencies to render channels unique. Its multiplexing function can be applied to a single channel, one that has already been separated into 24 channels by a multiplexer.

(b.) It can be used on a single T-1 channel, a fractional T-1, or a T-1.

(c.) It can be applied to any digital transmission protocol.

(d.) It can be applied to any medium capable of carrying electronically-coded digital information.

(e.) It can carry a large number of unique voice and data channels on a single line.

(f.) It does not render channels unique by using time division, for such division has severe limitations.

(g.) It does not rely on compression to increase bandwidth, and it is not subject to the limitation of using algorithms.

(h.) it provides an inexpensive means of increasing bandwidth.

While there has been shown a preferred embodiment of a system and method of disharmonic frequency multiplexing, it is to be understood that many changes may be made therein without departing from the spirit of the invention.

Thus the PFC multiplexing system and method can be applied not only to the communication of digital information, but also to its storage in which a plurality of digital information streams in the form of a disharmonic chord are stored in a CD ROM or other storage medium.

I claim:

1. A method for increasing transmission bandwidth for use with a computer processor and a mechanism for transmitting a plurality of simultaneous digital streams of information over a shared transmission medium, the method including the steps of:

a. converting incoming streams of binary information, in the form of "0"s and "1"s on each of a plurality of lines, into corresponding digitally-represented streams of "no-play" and "play" commands;

b. rendering the information in each of the plurality of incoming lines unique by assigning to each "no-play" and "play" command of a respective incoming line, a corresponding prime number Hertz frequency component, so as to provide a plurality of prime number Hertz frequency component streams;

c. simultaneously transmitting the unique prime number Hertz frequency component streams of each of the plurality of incoming lines over the shared transmission medium in the form of a "disharmonic" chord; and d. receiving the transmitted chord and separating each of the plurality of lines contained therein, so as to convert each of the plurality of lines into streams of binary information in the form of "0"s and "1"s, by programming each line to receive only digitally-represented audio bits corresponding to the prime number Hertz frequency component assigned thereto.

2. The method set forth in claim 1, further including the step of restoring the digital coding of each line back to its binary form by converting the digitally-represented stream of 'play" and "no-play" commands to a binary stream of "1"s and "0"s.

3. The method of claim 1 wherein said method is integrated into the software programming of a data or telecommunications switching device or server.

4. The method of claim 1 wherein said method is programmed onto an integrated circuit chip, and integrated into the hardware design and function of a data or telecommunications switching device or server.

5. The method of claim 1, wherein said method is used as part of an IP server that transmits voice over IP data lines, as used in Internet Telephony devices.

6. The method claim 1, wherein said method is used to compress and store digital information on devices including magnetic tape, CDS, computer hard drives, and computer memory chips.

7. The method of claim 1, wherein said method is used to transmit digital information over a voice and data transmission media including T-1, frame relay, satellite, ATM, and fiber optics.

8. The method of claim 1, wherein said method is used in the construction of computer microprocessors.

9. The method of claim 8, method is used to create megabit computer processing chips or computer processing chips of a determinable bit size.

10. The method of claim 9 wherein said method is used to create a computer processing chip where the size of the bit processor is not limited to 64 bits, or 128 bits, but to any size as determined by programming into the computer chip a specific number of instructions that the chip can deliver.

11. The method of claim 9 further including the step of allocating transmission instructions to a processor of any size, including but not limited to a 100 bit processor, a 1,000 bit processor, and/or a 10,000 bit processor.

12. The method of claim 1, wherein computer and machine instructions in digital coding are performed using prime number Hertz frequencies.

13. The method of claim 1, wherein said method is used to store and/or transmit digital information representing video, images, data and/or voice.

* * * * *